United States Patent [19] [11] 4,158,660
Gavin et al. [45] Jun. 19, 1979

[54] PROCESS FOR PRODUCING A PURIFIED 3,4-TOLUENEDIAMINE PRODUCT AND A MIXTURE OF 4- AND 5-METHYLBENZOTRIAZOLES FROM A MIXTURE OF ORTHO-TOLUENEDIAMINE ISOMERS

[75] Inventors: David F. Gavin, Cheshire, Conn.; Alan E. Ardis, San Diego, Calif.; Lawrence E. Katz, Orange, Conn.; John D. Schellberg, Downers Grove, Ill.

[73] Assignee: Olin Corporation, New Haven, Conn.

[21] Appl. No.: 880,837

[22] Filed: Feb. 24, 1978

[51] Int. Cl.² .................................... C07D 249/18
[52] U.S. Cl. .............................. 260/308 B; 260/582
[58] Field of Search ............................... 260/308 B

[56] References Cited

U.S. PATENT DOCUMENTS

| | | |
|---|---|---|
| 3,149,162 | 9/1964 | Gardner et al. ............... 260/582 |
| 3,732,239 | 5/1973 | Spatz et al. ................. 260/308 B |
| 3,960,963 | 6/1976 | Gavin .......................... 260/582 |

Primary Examiner—Paul M. Coughlan, Jr.
Attorney, Agent, or Firm—William A. Simons; Thomas P. O'Day

[57] ABSTRACT

A process for producing a purified 3,4-toluenediamine product and a mixture of 4- and 5-methylbenzotriazoles from a mixture of ortho-toluenediamine isomers, the process having the steps of (a) dissolving a mixture of ortho-toluenediamine isomers in water to form an aqueous solution;
(b) cooling the aqueous solution to a temperature whereby crystals of a purified 3,4-toluenediamine product are formed in an aqueous mother liquor;
(c) separating the purified 3,4-toluenediamine product crystals from the aqueous mother liquor;
(d) reacting the aqueous mother liquor with a diazotization agent selected from sodium nitrite, potassium nitrite, nitrous acid and nitrous anhydride in the presence of acetic acid to form a reaction mixture containing a mixture of 4- and 5-methylbenzotriazoles; and
(e) recovering the mixture of 4- and 5-methylbenzotriazoles from the reaction mixture.

13 Claims, 1 Drawing Figure

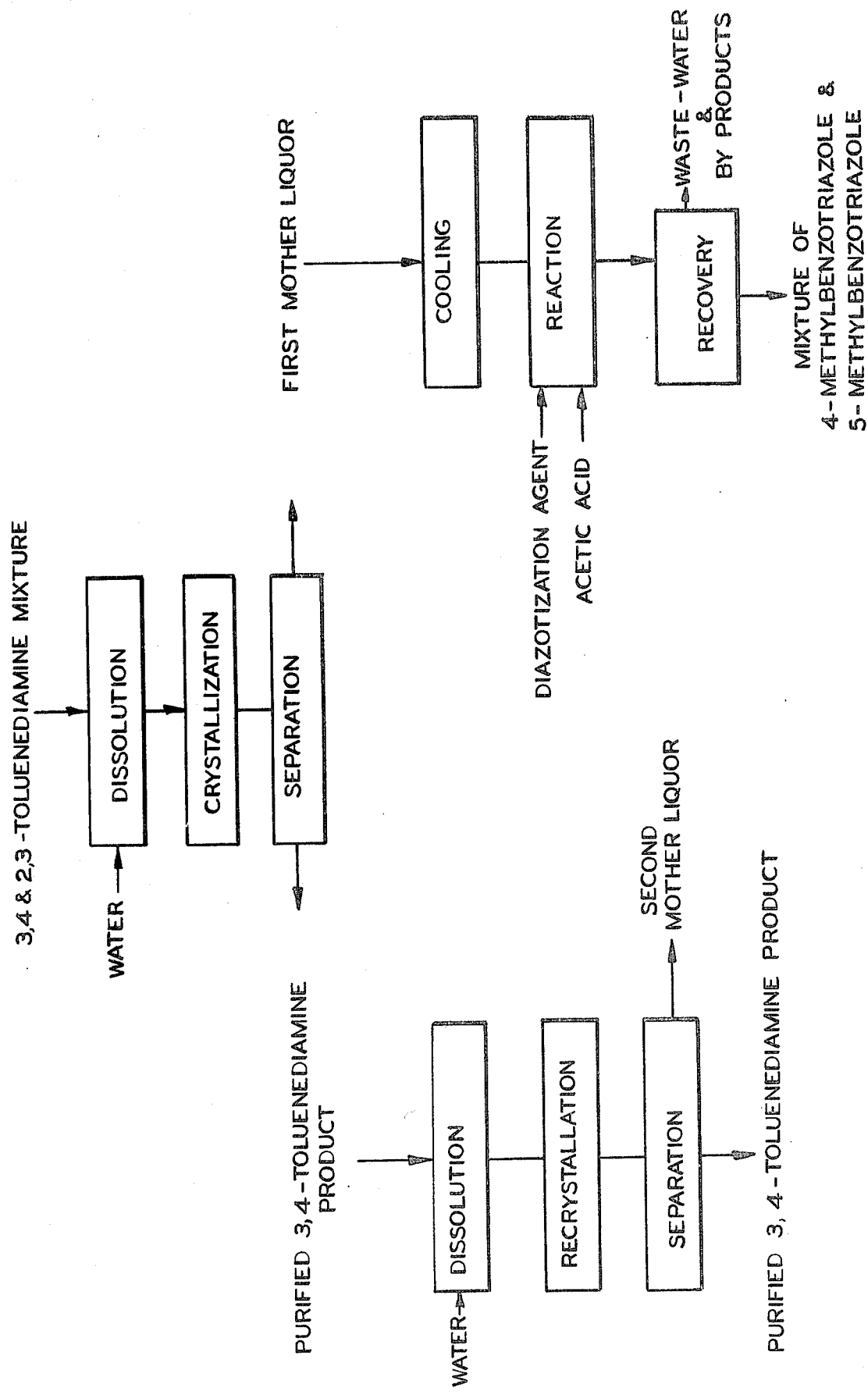

PROCESS FOR PRODUCING A PURIFIED 3,4-TOLUENEDIAMINE PRODUCT AND A MIXTURE OF 4- AND 5-METHYLBENZOTRIAZOLES FROM A MIXTURE OF ORTHO-TOLUENEDIAMINE ISOMERS

BACKGROUND OF THE INVENTION

1. Field of the Invention

The present invention relates to a process for the separation and recovery of a purified 3,4-toluenediamine product from an ortho-toluenediamine isomer mixture containing 2,3- and 3,4-toluenediamines. Furthermore, the present invention simultaneously relates to a process for producing a mixture of 4- and 5-methylbenzotriazoles from this 2,3- and 3,4-toluenediamine mixture.

2. Description of the Prior Art

Toluene diisocyanate (TDI), a valuable intermediate in the preparation of polyurethanes, is generally produced today by a multi-step process. This widely used process includes the steps of dinitrating toluene to produce a mixture of ortho- and meta-dinitrotoluene isomers, reducing this isomer mixture to form a mixture of ortho- (i.e., 2,3- and 3,4-, and meta- (i.e., 2,4- and 2,6-) toluenediamine isomers, separating the desired meta-isomers from the by-product ortho-isomers, and finally reacting these meta-isomers with phosgene to produce toluene diisocyanate. The separation of the desired 2,4- and 2,6-toluenediamine isomers from the by-product ortho-isomer fraction has been normally carried out by fractional distillation as disclosed in U.S. Pat. Nos. 3,637,514 and 3,732,239, both issued to Spatz et al on Jan. 25, 1972 and May 8, 1973, respectively, or by crystallization techniques in the presence of a selected solvent as disclosed in U.S. Pat. No. 3,149,162, issued to Gardner et al on Sept. 15, 1964.

Several million pounds of this ortho-toluenediamine by-product fraction is produced annually in the United States. But, because only limited amounts of this ortho-isomer mixture can be converted into commercial products such as corrosion inhibitors in antifreezes and the like, a substantial amount of this by-product must be disposed of, usually by burning.

In recent years, it has been discovered that relatively pure amounts of 3,4-toluenediamine may be employed in the synthesis of various heterocyclic compounds such as benzimidazoles, quinoxalines, and phenazines, whereas the above-mentioned commercially available ortho-toluenediamine isomer mixture cannot be so employed. Therefore, those persons working in this art have been desirous of a practical process that will separate the 2,3- and 3,4-isomers (sometimes referred to hereinafter as 2,3-TDA and 3,4-TDA) and then separately utilize them. Such a process could greatly benefit the overall TDI manufacturing operation since it would open up commercial uses for by-product, much of which must now be burned.

One process, disclosed in U.S. Pat. No. 3,960,963, issued to Gavin on June 1, 1976, does disclose a crystallization process for separating 2,3- and 3,4-toluenediamine isomers. In particular, this patented process dissolves a mixture of the isomers in either benzene, toluene, or xylene. While this patent does disclose a process which produces a very pure 3,4-toluenediamine product, there are presently no known uses for the 2,3-isomer product left in the organic solvent, and therefore, normally this 2,3-isomer product/organic solvent mixture is usually disposed of by burning. Furthermore, there are other practical difficulties with this Gavin process. For example, strict environmental regulations today normally prevent the large-scale burning of organic solvents like benzene, toluene or xylene. Also, the cost of burning these solvents will usually make the over-all process uneconomical. Moreover, the evaporation of the 2,3-isomer from these organic solvents is impractical since this isomer when out of solution decomposes readily and thus is unusable.

As mentioned in the Gavin patent, crystallization techniques are generally only used where it is desired to separate a pure component from a mixture containing the component and a minor amount of an impurity (usually 5% by weight of the mixture or less). Normally, however, where the impurity constitutes more than a minor amount of the mixture, one skilled in the art would not expect crystallization to be an effective tool to separate the desired component from the mixture. Thus, it would be expected that the use of crystallization techniques would not produce a desired degree of separation. Furthermore, it would be surprising that a widely used non-organic solvent such as water would be effective to dissolve aromatic compounds like these ortho-toluenediamine isomers as much as it has been found to by the present invention. Thus, it was quite unexpected and surprising to find that when commercially available ortho-toluenediamine isomer mixtures which contain about 40% to about 70% by weight 3,4-toluenediamine and about 30% to about 60% by weight 2,3-toluenediamine was dissolved in water and cooled, a substantially pure 3,4-toluenediamine crystalline product was obtained in high yields.

BRIEF SUMMARY OF THE INVENTION

The present invention is directed toward a process for producing a purified 3,4-toluenediamine product and a mixture of 4- and 5-methylbenzotriazoles from a mixture of ortho-toluenediamine isomers, the process having the steps of (a) dissolving a mixture of ortho-toluenediamine isomers in water to form an aqueous solution;

(b) cooling the aqueous solution to a temperature whereby crystals of a purified 3,4-toluenediamine product are formed in an aqueous mother liquor;

(c) separating the purified 3,4-toluenediamine product crystals from the aqueous mother liquor;

(d) reacting the aqueous mother liquor with a diazotization agent selected from sodium nitrite, potassium nitrite, nitrous acid and nitrous anhydride in the presence of acetic acid to form a reaction mixture containing a mixture of 4- and 5-methylbenzotriazoles; and (e) recovering the mixture of 4- and 5-methylbenzotriazoles from the reaction mixture.

DESCRIPTION OF THE DRAWING

The FIGURE describes a flow chart of a preferred embodiment of the present invention wherein a purified 3,4-toluenediamine product is formed by a two-stage crystallization process and wherein a mixture of 4- and 5-methylbenzotriazoles is formed by reacting the first mother liquor with a diazotization agent in the presence of acetic acid.

DETAILED DESCRIPTION

The usual starting material for the present invention is a mixture of ortho-toluenediamine isomers obtained as a by-product after separation from the 2,4- and 2,6-toluenediamine isomers during the manufacture of toluene diisocyanate (TDI). This ortho-isomer mixture usually contains from about 40% to about 70%, preferably about 50% to about 60%, by weight of 3,4-toluenediamine and about 30% to about 60%, preferably about 35% to about 50%, by weight of 2,3-toluenediamine.

In addition, one may find various impurities present in the starting mixture depending on the precise conditions under which it was prepared. The major impurity usually found in this mixture is the meta-toluenediamine isomers (i.e., 2,4- and 2,6-isomers). These meta-isomers may be present in amounts ranging from 0% up to about 30% by weight of the starting mixture. Preferably, however, the amount of these meta-isomers is limited to about 15% by weight. Other impurities which may be present include, inter alia, nitrotoliudines, unreacted toluene and nitrotoluenes, but these are generally present in minor amounts, for example, no more than about 0.2% by weight and have no noticeable effect on the present process. Generally, the starting material contains from about 70% to 100% by weight mixed ortho-toluenediamines, more usually, from about 85% to 100% by weight.

While the present invention is primarily directed to starting with the by-product of the above-described toluene diisocyanate process, it may also encompass separation of 3,4-toluenediamine from mixtures of ortho-toluenediamine isomers resulting from production of other chemicals and in fact is applicable to any mixture containing the 2,3- and 3,4-isomers in the suitable proportions described above.

In accordance with the present invention, the mixture of ortho-toluenediamine isomers is first dissolved in water. The amount of water necessary for the purpose of dissolving the ortho-toluenediamine mixture may be any suitable amount and may depend upon the temperature at which crystallization is to be commenced and upon the proportions of 3,4- and 2,3-isomers in the ortho-toluenediamine mixture. It has been found that a weight ratio of water to the ortho-toluenediamine mixture in the range of about 3:1 to about 8:1 is preferred. More preferred is the range of this weight ratio from about 4:1 to about 6:1. Most preferred is a range of about 4:1 to about 5:1.

As noted above, the ortho-toluenediamine mixture may contain certain impurities and some of these may be insoluble in water. If such insoluble impurities are present, it is desirable that these be removed, for example, by filtration, before cooling to a point at which precipitation by crystallization begins to occur. In most situations, however, the by-product diamine mixture will be completely soluble and this filtration step will not be required.

This isomer mixture may be dissolved in water at any desired temperature. It is preferable, however, to select a temperature below the boiling point of water to minimize evaporation and loss of solvent. Alternatively, of course, the dissolution in water and/or crystallization may be carried out under pressure but such a procedure, while suitable, is not preferred since it merely increases the cost of the process without providing any major advantage.

It is preferred to employ a dissolution temperature above ambient temperature (e.g., from about 50° C. to about 100° C.) if possible. By employing an elevated temperature for dissolution, the necessity for forced cooling of the diamine/water mixture during the following crystallization step is generally avoided. While lower dissolution temperatures may be employed, no advantage is seen in utilizing the same and it is highly likely that the supplemental cooling for crystallization which may then be required would merely increase processing costs.

Following dissolution of the ortho-toluenediamine isomer mixture in water, the resulting aqueous solution is cooled to a temperature at which 3,4-toluenediamine crystals begin to precipitate out of the solvent. Such precipitation usually occurs in the temperature range of about 50° C. and lower, but will depend on the dissolution temperature employed above and on other factors. It is quite surprising to find with water as the solvent that one could crystallize out a purified 3,4-toluenediamine product instead of the mixture of 2,3- and 3,4-toluenediamine isomers on a proportional basis.

As employed herein, the term "purified 3,4-toluenediamine product" means a product which exceeds about 80%, preferably 90%, by weight 3,4-toluenediamine when dried. With water as the solvent for this crystallization technique, the purity of the resulting purified 3,4-toluenediamine product is not as high as with toluene, xylene or benzene as disclosed in the Examples of the above-mentioned U.S. Pat. No. 3,960,963 (i.e., above about 97% by weight purity), but the purity of the present product after one crystallization is normally above about 85% by weight, usually in the range of from about 85% to about 95%.

Thus, having cooled to the point at which precipitation commences, the cooling may be continued to considerably lower temperatures, for example, to temperatures in the range of about −5° C. to about 35° C. The present process of believed to have certain advantages over the crystallization process disclosed in U.S. Pat. No. 3,960,963. For example, the employment of water as the solvent does not lead to a great temperature dependency for increasing yields as with the organic solvents disclosed in that patent. Thus, one does not have to continue cooling to a relatively low temperature, such as less than −10° C., to achieve high yields of purified product.

While it is possible to continue cooling to very low temperatures, some point will be reached for each aqueous solution at which 2,3-toluenediamine will begin to drop out in amounts which exceed desirable limits. While this point will be dependent on the factors discussed above, it is believed to be preferable not to cool substantially below 0° C. since this, in addition to producing a less pure product, it may also result in the crystallization of the water into ice.

When cooling is completed, the precipitated crystals are separated from the mother liquor by any suitable means, for example, filtration, and dried to provide a purified 3,4-toluenediamine product which as stated above, contains at least about 80%, preferably at least about 90%, by dry weight of 3,4-toluenediamine.

In a preferred embodiment of the process of the present invention, the purified 3,4-toluenediamine product is further purified by subjecting it to one or more recrystallization procedures. As shown on the FIGURE, such a recrystallization procedure may include exactly the same steps as the above-described crystallization sequence, namely, the steps of dissolution, crystallization by cooling, and finally followed by a separation step. As stated above, the resulting purified 3,4-toluenediaine product without such recrystallization normally contains from about 85% to about 95% by weight of the 3,4-toluenediamine isomer, although its purity in some cases may be greater. By subjecting this purified product to a second crystallization procedure, the 3,4-toluenediamine content in the final product can normally be raised up to about 97% by weight or greater. More than two crystallization procedures may be used to obtain an even more purified 3,4-toluenediamine product, but this would normally be impractical for most commercial processes.

Furthermore, according to the present process, the first aqueous mother liquor, either alone or in combination with the mother liquors of subsequent recrystallization steps, is utilized as a starting material for the production of a mixture of 4- and 5-methylbenzotriazoles (also known as 4-methyl-2H-benzotriazole and 5-methyl-2H-benzotriazole, or simply as mixed tolytriazoles). Note Equation I, below, generally illustrates this reaction. The term "mixture of 4- and 5-methylbenzotriazoles" as employed in the specification and claims herein refers to any of the tautomeric forms of either 4-methylbenzotriazole or 5-methylbenzotriazole. The first mother liquor contains a major portion of the 2,3-TDA originally present in ortho-toluenediamine isomer mixture and the remainder of the 3,4-TDA which was not precipitated and recovered by the above-described crystallization procedure. This first mother liquor may also contain some of the impurities originally present in the starting isomer mixture. The second mother liquor normally contains less 2,3-TDA and other impurities than the first mother liquor.

Either or both of these mother liquors are reacted with a selected diazotization agent and acetic acid to form the mixture of 4- and 5-methylbenzotriazole.

The usual diazotization agents, namely, sodium nitrite, potassium nitrite, nitrous anhydride, and nitrous acid, may be employed in the reaction and the nitrous acid may be prepared in situ by any known method, for example, by dissolving an alkali metal nitrite in excess hydrogen fluoride. Normally, from about 1.0 to about 1.5 moles of the diazotization agent, preferably from about 1.0 to about 1.25, are employed per combined moles of 2,3- and 3,4-toluenediamine present.

Acetic acid acts both as the source of hydrogen ion for the reaction and possibly as means for adjusting the pH of the reaction medium. Suitably, from about 1 mole up to about 10 moles, preferably from 2 moles up to about 5 moles, of acetic acid are employed per mole of ortho-toluenediamine isomers present in said mother liquor or liquors.

Instead of acetic acid, it may be desirable to employ other equivalent acids such as propionic and butyric acids. However, acetic acid is preferred because of its low cost and good effectiveness in the present reaction. Halogen-containing acids such as HCl, HF, HBr and HI are not desirable as substitutes for acetic acid in the present process because they may result in undesirable reactions.

The generalized reaction for producing tolytriazole according to the present invention is illustrated by the following reaction wherein sodium nitrite is employed as the diazotization agent:

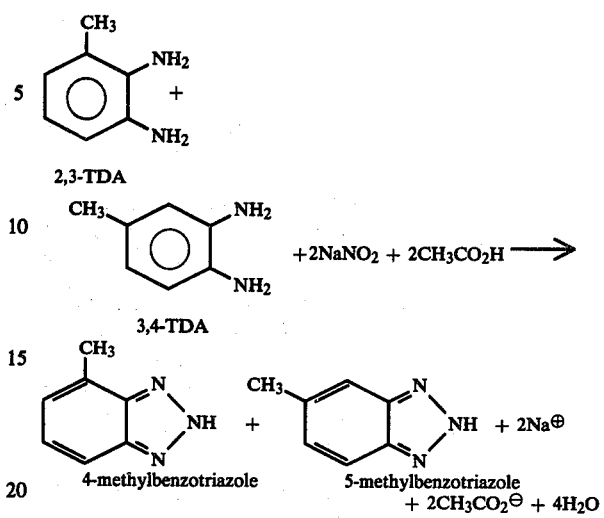

Preferably, the reaction is carried out by first cooling the mother liquor to a relatively low temperature in the range of about 0° C. to about 20° C., more preferably to 0° C. to 10° C. This cooling prevents an uncontrolled reaction from occuring when the other reactants are combined with the aqueous mother liquor. Preferably, after this cooling, acetic acid and a selected diazotization agent are added to the mother liquor. Normally, an exotherm immediately occurs which raises the temperature of the reaction mixture to a range from about 25° C. to about 50° C. Next, the reaction mixture is heated to a temperature of about 60° C. to about 100° C., more preferably from about 70° C. to about 90° C. to effect cyclization of the 4- and 5-methylbenzotriazole.

The desired mixture of 4- and 5-methylbenzotriazoles is next recovered from the reaction mixture by any suitable method. In one preferred recovery method, the reaction mixture is first cooled to below about 30° C. to solidify at least a major portion (i.e., 50% by weight) of 4- and 5-methylbenzotriazoles contained therein. Cooling the reaction mixture, after the formation of these desired products is complete, causes the precipitation of solid product of 4- and 5-methylbenzotriazoles from the aqueous reaction suspension. This solid product is easily separated from the aqueous portion of the reaction mixture by any conventional technique such as filtration, decantation, centrifugation, or any suitable methods of removing a solid from a liquid. The aqueous portion may be then extracted with a suitable organic solvent such as chloroform, benzene, ether, methylene chloride, or toluene, or mixtures thereof to extract any remaining product out of the aqueous phase and into the organic phase. Most preferably, the aqueous phase is discarded and the organic phase is then evaporated to yield more desired product. Subsequently, this latter product may be combined with the first solid 4- and 5-methylbenzotriazole product. Next, one or both of these solid products may be distilled to remove any low-boiling impurities such as residual water and non-distillables such as tars, normally yielding a substantially pure mixture of 4- and 5-methylbenzotriazoles (i.e., more than 95% by weight, more likely greater than 99% by weight, pure).

This recovered product can be utilized as an antioxidant for many applications such as for photographic film and as corrosion inhibitors in antifreeze mixtures.

The following examples further illustrate the present invention. All percentages are by weight unless expressly stated otherwise.

EXAMPLE I

A mixture of 1 Kgm ortho-toluenediamine isomers (57.4% 3,4-TDA, 36.9% 2,3-TDA) and 4 l of water was heated with stirring to 84° C. This was allowed to cool to room temperature overnight with stirring. The product was filtered on a Buchner funnel with suction and pressed dry with a rubber dam. The yield of partially dried (35.4% water) TDA (84.4% 3,4-TDA, 15.6% 2,3-TDA) was 817 gms (a 77.5% recovery of 3,4-TDA).

This purified 3,4-toluenediamine product was mixed with 3050 ml of water and was reheated with stirring to 85° C. This was allowed to cool to room temperature overnight with stirring. The product was filtered on a Buchner funnel with suction, washed with 870 ml of ice water and pressed with a rubber dam. The yield of tan solid (56% water) was 700 gms (a 52.8% recovery of 3,4-TDA overall) which assayed at 98.5% 3,4-TDA.

EXAMPLE II

A mixture of 200.5 gms ortho-toluenediamine isomers (58.8% 3,4-TDA, 40.3% 2,3-TDA) and 1 l of hot (80° C.) water was stirred overnight. The mixture was cooled to 10° C., filtered on a Buchner funnel with suction and pressed dry with a rubber dam. The yield of partially dried (24.5% water) TDA (89.1% 3,4-TDA, 9.4% 2,3-TDA) was 112.7 gms (a 64.3% recovery of 3,4-TDA).

The mother liquor was cooled to 5° C. and 114 gms of acetic acid added. An aqueous solution of 72.4 gms of sodium nitrite was added all at once with stirring and the ice bath removed. The temperature rose to 37° C. and the solution was then heated to 82° C. on a steam bath with stirring. This was stirred for two hours while the mixture cooled to room temperature. A red-brown solid precipitated out and was filtered off. The aqueous solution was extracted with 250 ml of chloroform and the chloroform solution rotary evaporated to yield an oil. The oil was combined with the dried solid to give 120.1 gms of a crude mixture of 4-methylbenzotriazole and 5-methylbenzotriazole. This was distilled under vacuum, bp 128°–139° C., (at 0.15–0.25 mm of Hg) to give 102.2 gms of a substantially pure mixture of these isomers.

What is claimed is:

1. A process for producing a purified 3,4-toluenediamine product and a mixture of 4- and 5-methylbenzotriazoles from a mixture of ortho-toluenediamine isomers comprising about 40% to about 70% by weight 3,4-toluenediamine isomer and about 30% to about 60% by weight 2,3-toluenediamine isomer, said process comprising the steps of
    (a) dissolving said mixture of ortho-toluenediamine isomers in water to form an aqueous solution;
    (b) cooling said aqueous solution to a temperature whereby crystals of a purified 3,4-toluenediamine product are formed in an aqueous mother liquor;
    (c) separating said purified 3,4-toluenediamine product from said aqueous mother liquor;
    (d) reacting said aqueous mother liquor with a diazotization agent selected from sodium nitrite, potassium nitrite, nitrous acid and nitrous anhydride in the presence of acetic acid to form a reaction mixture containing a mixture of 4- and 5-methylbenzotriazoles;
    (e) recovering at least a portion of said 4- and 5-methylbenzotriazoles from said reaction mixture.

2. The process of claim 1 wherein said purified 3,4-toluenediamine product is further purified by
    (f) adding water to said purified 3,4-toluenediamine product to form a second aqueous solution;
    (g) cooling said second aqueous solution to form crystals of a purified 3,4-toluenediamine product; and
    (h) separating said purified 3,4-toluenediamine product from said second aqueous solution.

3. The process of claim 1 wherein said 4- and 5-methylbenzotriazoles are recovered in step (e) by
    (i) cooling said reaction mixture to below about 30° C. to solidify at least a portion of the 4- and 5-methylbenzotriazoles;
    (ii) removing said solidified 4- and 5-methylbenzotriazoles from said reaction mixture; and
    (iii) distilling said solidified 4- and 5-methylbenzotriazoles to remove residual water and impurities therefrom.

4. The process of claim 1 wherein said reaction of step (d) is carried out by cooling said aqueous mother liquor to a temperature in the range of about 0° C. to about 20° C., adding said acetic acid and said diazotization agent to said cooled mother liquor and heating the resulting reaction mixture to a temperature of about 60° C. to about 100° C.

5. The process of claim 4 in which said ortho-toluenediamine mixture produced by dinitrating toluene, reducing the resulting dinitrotoluenes and distilling the resulting mixture.

6. The process of claim 5 wherein from about 1.0 to 1.5 moles of diazotization agent are employed per the combined moles of 2,3- and 3,4-toluenediamine present in said mother liquor.

7. The process of claim 6 wherein from about 1 mole to about 10 moles of acetic acid are employed per combined moles of 2,3- and 3,4-toluenediamine present in said mother liquor.

8. The process of claim 7 wherein the weight ratio of said water to said mixture of ortho-toluenediamine isomers in step (a) is in the range of about 3:1 to about 8:1.

9. The process of claim 8 wherein said diazotization agent is sodium nitrite.

10. The process of claim 9 wherein said mixture is dissolved in step (a) at a temperature in the range from about 50° C. to about 100° C.

11. The process of claim 10 wherein said mixture is cooled in step (b) to a temperature in the range of from about −5° C. to about 35° C.

12. The process of claim 11 wherein said purified 3,4-toluenediamine product is further purified by
    (f) adding water to said purified 3,4-toluenediamine product to form a second aqueous solution;
    (g) cooling said second aqueous solution to form crystals of a purified 3,4-toluenediamine product;
    (h) separating said purified 3,4-toluenediamine product from said second aqueous solution.

13. The process of claim 12 wherein said 4- and 5-methylbenzotriazoles are recovered in step (e) by 30° C. to solidify at least a portion of the 4- and 5-methylbenzotriazoles;
    (ii) removing said solidified 4- and 5-methylbenzotriazoles from said reaction mixture; and
    (iii) distilling said solidified 4- and 5-methylbenzotriazoles to remove residual water and impurities therefrom.

* * * * *

UNITED STATES PATENT AND TRADEMARK OFFICE
CERTIFICATE OF CORRECTION

PATENT NO. : 4,158,660

DATED : June 19, 1979

INVENTOR(S) : David F. Gavin, Alan E. Ardis, Lawrence E. Katz & John D. Schellberg It is certified that error appears in the above-identified patent and that said Letters Patent are hereby corrected as shown below:

In Column 4, line 34, "of" should read --is--.

In Column 7, line 7, "4 1" should read --4 $\underline{1}$--.

In Column 7, line 25, "1  1" should read -- 1  $\underline{1}$ --.

In Column 8, line 60, after "by" insert --(i) cooling said reaction mixture to below about--.

Signed and Sealed this

*Twenty-seventh* Day of *November 1979*

[SEAL]

Attest:

RUTH C. MASON
*Attesting Officer*

LUTRELLE F. PARKER
*Acting Commissioner of Patents and Trademarks*